United States Patent [19]
Carver et al.

[11] Patent Number: 5,972,992
[45] Date of Patent: *Oct. 26, 1999

[54] INJECTABLE COMPOSITION

[75] Inventors: David Carver, Boulder; Timothy Prout, Erie; Hernita Ewald, Denver, all of Colo.; Robyn Elliott, Lanctwarrin; Paul Handreck, Glen Iris, both of Australia

[73] Assignee: NaPro Biotherapeutics, Inc., Boulder, Colo.

[*] Notice: This patent is subject to a terminal disclaimer.

[21] Appl. No.: 09/028,906

[22] Filed: Feb. 24, 1998

Related U.S. Application Data

[63] Continuation of application No. 08/594,478, Jan. 31, 1996, Pat. No. 5,733,888.

[51] Int. Cl.$^6$ .................................................. A01D 43/02
[52] U.S. Cl. .......................................................... 514/449
[58] Field of Search .............................................. 514/449

[56] References Cited

U.S. PATENT DOCUMENTS

| | | | |
|---|---|---|---|
| 3,864,370 | 2/1975 | Yamashito et al. | |
| 4,814,470 | 3/1989 | Colin et al. | 514/449 |
| 4,942,184 | 7/1990 | Haugwitz et al. | 414/449 |
| 4,960,790 | 10/1990 | Stella et al. | 519/449 |
| 5,157,049 | 10/1992 | Haugwitz et al. | 514/449 |
| 5,254,580 | 10/1993 | Chen et al. | 514/449 |
| 5,281,727 | 1/1994 | Carver et al. | |
| 5,391,385 | 2/1995 | Seybold. | |
| 5,403,858 | 4/1995 | Bastard | 514/471 |
| 5,504,102 | 4/1996 | Agharkar et al. | 514/449 |
| 5,733,888 | 3/1998 | Carver et al. | 514/449 |

FOREIGN PATENT DOCUMENTS

| | | |
|---|---|---|
| 32861 | 1/1989 | Australia. |
| 428376 | 5/1991 | European Pat. Off.. |
| 505047 | 2/1992 | European Pat. Off.. |
| 522936 | 1/1993 | European Pat. Off.. |
| 522937 | 7/1993 | European Pat. Off.. |
| 9010443 | 9/1990 | WIPO. |
| 9412198 | 6/1994 | WIPO. |

OTHER PUBLICATIONS

Dordunoo, Stephen K., and Helen M. Burt (1996) "Solubility and Stability of Taxol: Effects of Buffers and Cyclodextrins" International Journal of Pharmaceutics 133: 191–201.

Kingston, David, G.I., Neal F. Magri, Chote Jitrangsri (1986) "Synthesis and Structure–Activity Relationships of Taxol Derivatives as Anticancer Agents" Studies in Organic Chemistry 26:219–235.

Kingston, David G. I. (1991) The Chemistry of Taxol: Pharmac. Ther. 52:1–34.

Longnecker, et al. (1987) "High Performance Liquid Chromatographic Assay of Taxol in Human Plasma and Pharmacokinetics in Phase I Trial" Cancer Treatment Reports 71(1).

Magri, Neal F. and David G. I. Kingston (1986) "Modified Taxols. 2. Oxidation Products of Taxol" Journal of Org. Chem. 51:797–802.

Mathew, A. E. M. Mejillano, J. P. Nath, R. H. Himes, and V. J. Stella (1992) "Synthesis and Evaluation of Some Water Soluble Prodrugs and Derivatives of Taxol and Antitumor Activity," J. Med. Chem. 35:145–51.

Richheimer, Steven L., David M. Tinnermeier and Daniel W. Timmons (1992) "High Performance Liquid Chromatographic Assay of Taxol" Anal. Chem. 64:2323–2326.

Ringel, Israel, Susan Band Horwitz (1987) "Taxol is Converted to 7–Epitaxol, a Biologically Active isomer, in Cell Culture Medium" Journal of Pharmacology and Experimental therapeutics 242(1):692–698.

Waugh, Wanda N., Lawrence A. Trissel and Valentino J. Stella (1991) "Stability , Compatibility, and Plasticizer Extraction of Taxol (NCS–125973) Injection Diluted in infusion Solutions and Stored in Various Containers" Reports Taxol 48 1520–1524.

Rowinsky, E., et al. "Taxol: A Novel Investigational Antimicrotubule Agent" Journal of the National Cancer Institute (1990) 82(15): 1247–59.

Tarr, B. D. et al. "A New Parenteral Vehicle for the Administration of Some Poorly Soluble Anti–Cancer Drugs"J. Parenter. Sci. Technol. (1987) 41(1):31–33.

Trissel, Lawrence (1988) "Monographs on Digoxin, Edrophonium chloride, Etoposide, Hydromorphine Hcl, Methyldopate HC1, Metronidazole, Nalbupine HCl, Phenylephjrine HCl, and Vitamin A" Handbook on Injectable Drugs, 5$^{th}$ Edition.

Primary Examiner—Keith D. MacMillan
Attorney, Agent, or Firm—Saliwanchik, Lloyd & Saliwanchik

[57] ABSTRACT

A pharmaceutical formulation of taxol and polyethoxylated castor oil is disclosed to be stabilized by reducing its pH to less than 8.1 and preferably within a pH range of 5 to 7, inclusively. Ethanol is optionally included in the formulation which is adapted for use in a body for the treatment of cancer. A formulation method is disclosed and includes the step of reducing the pH of a carrier material, such as polyethoxylated castor oil, to form a carrier solution after which taxol is added in an amount such that the resulting pH is less than 8.1 and preferably in a pH range of 5 to 7. Ethanol may optionally be slurried with the taxol before mixing with the carrier solution.

15 Claims, No Drawings

INJECTABLE COMPOSITION

CROSS-REFERENCE TO RELATED APPLICATIONS

This application is a continuation application of co-pending application Ser. No. 08/594,478, filed Jan. 31, 1996 U.S. Pat. No. 5,733,888.

This invention relates to a solution of taxol having improved stability

BACKGROUND OF THE INVENTION

Taxol is a compound extracted from the bark of a western yew, *Taxus brevifolia* and known for its antineoplastic activity. It is described for example in The Merck Index, Eleventh Edition 1989, monograph 9049.

In 1977, taxol was chosen for development as an antineoplastic agent because of its unique mechanism of action and good cytotoxic activity against IP implanted D16 melanoma and the human X-1 mammary tumor xenograft. Taxol is believed to function as a mitotic spindle poison and as a potent inhibitor of cell replication in vitro. Other mitotic spindle points (colchicine and podophyllotoxin) inhibit microtubule assembly. Taxol employs a different mechanism of action since it appears to shift the equilibrium of polymerimization/depolymerization toward polymer assembly and to stabilize microtubules against depolymerization under conditions which would cause rapid disaggregation of microtubules. The interference with the polymerization/depolymerization cycle in cells appears to interfere with both the replication and migration of cells.

After extensive preclinical screening in mouse tumor models, taxol entered clinical trials in 1983. Over the past few years, taxol has demonstrated good response rates in treating both ovarian and breast cancer patients who were not benefiting from vinca alkaloid or cisplatin therapy. It has also shown encouraging results in patients with other types of cancer including lung, melanoma, lymphoma, head and neck.

For further information, reference may be made to the U.S. National Cancer Institute's Clinical Brochure for Taxol, revised July 1991, and papers presented at the Second National Cancer Institute Workshop on Taxol and Taxus held in Alexandria, Va. USA on Sep. 23–24, 1992.

BRIEF DESCRIPTION OF THE INVENTION

It is a disadvantage of the known formulation that the taxol therein degrades, with the result that the shelf life of the formulation is unsatisfactory, and there is therefore a need for a taxol solution of improved stability.

Accordingly, in a general aspect the invention provides a solution containing taxol, CREMOPHOR EL™ and ethanol, characterized in that the pH of the solution has been adjusted into the range 1 to 8 by addition of an acid.

Acids in the form of powders, for example citric acid, are preferred over those which contain water, for example sulfuric acid. The most preferred acid for use in accordance with the present invention is citric acid but a wide range of acids may be used including the following:

Citric acid—monohydrous
Citric acid—anhydrous
Citric acid—hydrous
Acetic acid
Formic acid
Ascorbic acid
Aspartic acid
Benzene sulphonic acid
Benzoic acid
Hydrochloric acid
Sulphuric acid
Phosphoric acid
Nitric acid
Tartaric acid
Diatrizoic acid
Glutamic acid
Lactic acid
Maleic acid
Succinic acid

DETAILED DESCRIPTION OF THE INVENTION

Due to its limited solubility in water, Taxol is usually prepared and administered in a vehicle containing CREMOPHOR EL™ (a polyethoxylated castor oil which acts as a solubilizer) and ethanol. A commercially available solution supplied by Bristol-Myers Squibb (BMS) is formulated with these components and has a pH of 9.1.

As indicated above, the invention essentially teaches addition of an acid to a taxol formulation to adjust its pH into the range 1 to 8, preferable 5 to 7.

In a preferred procedure adopted by the applicant, which it will be clearly understood is non-limiting, the following steps were carried out:

Mixing Instructions

Solution 1

Citric acid was dissolved in absolute alcohol, using a ratio of 8 mls of absolute alcohol to 1 gram of citric acid, and the solution was stirred for fifteen (15) minutes.

Solution 2

CREMOPHOR EL was weighed out into the main mixing vessel.

Solution 3

Solution 1 was added to solution 2, and the container used for solution 2 was washed with a minimum quantity of absolute alcohol to ensure complete transfer of the citric acid. Solution 3 was mixed and bubbled with nitrogen for at least 15 minutes. The taxol was weighed out and slurried using absolute alcohol, using a ratio of 8 ml of absolute alcohol to 1 gm of taxol. The slurried taxol was added to solution 3 and the slurrying vessel was washed with a minimum quantity of absolute alcohol. Solution 3 was adjusted to 75% of required volume using absolute alcohol, and thoroughly stirred for at least 45 minutes until completely dissolved. Once completely dissolved, the volume was checked and made up as necessary with absolute alcohol and the final solution stirred for 5 minutes.

EXAMPLE 1

A solution was prepared with the following formulation:

| Formulation: (Sample 1) | |
|---|---|
| CREMOPHOR | 0.5 mL |
| Citric Acid (Anhydrous) | 2.0 mg |
| Taxol | 6.0 mg |
| Absolute Alcohol to | 1.0 mL |

The pH of this solution was determined as 6.1.

The stability of this sample was compared with a sample prepared by the formulation stated in the NCI Taxol Clinical brochure (as follows) which had a pH of 9.1. (Sample 2)

| Sample 2 | per mL |
|---|---|
| Taxol | 6 mg |
| CREMOPHOR | 0.5 mL |
| Absolute Alcohol | to 1 mL |

The solutions were filled into clear type 1 glass 5 mL vials and sealed with rubber bungs.

The solutions were stored at 40° C. for 7 (seven) days and the stability results are shown in Table 1.

|  | Sample 1 | Sample 2 |
|---|---|---|
| pH | 6.2 | 9.0 |
| Potency | 96.6 | 86.7 |
| Major individual impurity | 0.3% | 5.1% |
| Total impurities | 2.0% | 12.2% |

Clearly Sample 1 showed significantly increased stability over Sample 2.

EXAMPLE 2

A solution was prepared with the following formulation:

| Formulation: (Sample 3) | |
|---|---|
| CREMOPHOR | 0.5 mL |
| Taxol | 6.0 mg |
| Absolute Ethanol | to 1 mL | pH adjusted to 6.6 with 1.0M Acetic Acid.

The solution was filled into clear type I glass 5 mL vials and sealed with rubber bungs.

The solution was stored at 40° C. for 7 days.

The stability results obtained are compared to those seen with Sample 2.

|  | Sample 3 | Sample 2 |
|---|---|---|
| pH | 6.7 | 9.0 |
| Potency | 97.5 | 86.7 |
| Major individual impurity | 0.3% | 5.1% |
| Total impurities | 2.3% | 12.2% |

Again the significantly superior stability of the formulation according to the invention (Sample 3) is evident.

It will be clearly understood that the invention in its general aspects is not limited to the specific details referred to hereinabove.

We claim:

1. A pharmaceutical taxol composition comprising taxol and a pharmaceutically-acceptable carrier wherein said pharmaceutical taxol composition has a pH less than or equal to 7.0.

2. The pharmaceutical taxol composition of claim 1 having a pH between 5 and 7, inclusive.

3. The pharmaceutical taxol composition of claim 1 further comprising ethanol as a constituent thereof.

4. The pharmaceutical taxol composition of claim 3 having a pH of between 5 and 7, inclusive.

5. The pharmaceutical taxol composition of claim 1, wherein said pharmaceutically-acceptable carrier is polyethoxylated castor oil.

6. The pharmaceutical taxol composition of claim 6, wherein said composition is anhydrous.

7. An improved method of formulating a pharmaceutical taxol solution, such that the taxol does not readily degrade, comprising the following steps:

mixing taxol with a carrier material to form a taxol solution; and reducing the pH of said taxol solution to a level whereby the taxol solution is stabilized such that at least 95% of the taxol potency is retained when the composition is stored at 40° C. for seven (7) days.

8. The method of claim 7, wherein said carrier material is polyethoxylated castor oil.

9. The method of claim 7 further comprising the step of slurrying said taxol in alcohol before mixing said taxol with the carrier material.

10. An article of manufacture comprising a container and a pharmaceutical formulation contained therein, said pharmaceutical formulation comprising a pharmaceutically-acceptable carrier and taxol, wherein said pharmaceutical formulation has a pH of about 7 or less.

11. The article of manufacture of claim 10, wherein said pharmaceutically-acceptable carrier is polyethoxylated castor oil.

12. The article of manufacture of claim 10, wherein said pharmaceutical formulation further comprises ethanol.

13. The article of manufacture of claim 10, wherein said pharmaceutical formulation has a pH between 5 and 7, inclusive.

14. The article of manufacture of claim 10 further comprising instructions for administering said pharmaceutical formulation to a patient.

15. A pharmaceutical taxol composition comprising:

taxol;

polyethoxylated castor oil; and ethanol, wherein said taxol composition has a pH sufficient to improve the stability of said taxol such that at least 95% of the taxol potency is retained when the composition is stored at 40° C. for seven (7) days.

* * * * *

UNITED STATES PATENT AND TRADEMARK OFFICE
CERTIFICATE OF CORRECTION

PATENT NO. : 5,972,992
DATED : October 26, 1999
INVENTOR(S) : David L. Carver, Timothy Prout, Hernita Ewald, Robyn Elliott, and Paul Handreck It is certified that error appears in the above-identified patent and that said Letters Patent is hereby corrected as shown below:

On the title page, item [63] after "Patent No. 5,733,888" insert
-- , which is a continuation of application No. 07/995,501, filed December 22, 1992, now abandoned. --.

please insert Item [30],
--Related Foreign Application Data
  November 27, 1992 Australian Patent No. 6074. --.

Column 2, line 61: "CREMOPHOR" should read --Cremophor EL--.

Column 3, line 8: "CREMOPHOR" should read --Cremophor EL--;

line 32: "CREMOPHOR" should read --Cremophor EL--.

Column 4, line 15: "claim 6" should read --claim 1--.

Signed and Sealed this

Twelfth Day of December, 2000

Attest:

Q. TODD DICKINSON

*Attesting Officer*      *Director of Patents and Trademarks*

UNITED STATES PATENT AND TRADEMARK OFFICE
CERTIFICATE OF CORRECTION

PATENT NO. : 5,972,992
DATED : October 26, 1999
INVENTOR(S) : David L. Carver, Timothy Prout, Hernita Ewald, Robyn Elliott, and Paul Handreck It is certified that error appears in the above-identified patent and that said Letters Patent is hereby corrected as shown below:

column 1, line 7 after "U.S. Pat. No. 5,733,888" please insert the following:

--, which is a continuation of application no. 07/995,501, filed December 22, 1992, now abandoned; and which also claims priority under 35 USC §119 to Australian Patent No. 6074 filed November 27, 1992--.

Signed and Sealed this

Sixth Day of March, 2001

Attest:

NICHOLAS P. GODICI

*Attesting Officer*  *Acting Director of the United States Patent and Trademark Office*